United States Patent [19]

Schelhas

[11] Patent Number: 5,019,107
[45] Date of Patent: May 28, 1991

[54] PROSTHESIS FOR PARTIALLY REPLACING THE JOINT HEAD OF A HUMAN BONE

[75] Inventor: Klaus-Deiter Schelhas, Bremen, Fed. Rep. of Germany

[73] Assignee: Bristol-Meyers Squibb Company, New York, N.Y.

[21] Appl. No.: 507,154

[22] Filed: Apr. 10, 1990

[30] Foreign Application Priority Data

Apr. 18, 1989 [IT] Italy .................................. 3912653

[51] Int. Cl.$^5$ .......................... A61F 2/36; A61F 2/30
[52] U.S. Cl. ........................................ 623/23; 623/16; 623/18
[58] Field of Search ..................... 623/23, 22, 18, 16, 623/20, 21

[56] References Cited

U.S. PATENT DOCUMENTS

| 2,718,228 | 9/1955 | Steenbrugghe | 623/23 |
| 4,146,936 | 4/1979 | Aoyagi et al. | 623/23 X |
| 4,177,524 | 12/1979 | Grell et al. | 623/18 X |
| 4,312,079 | 1/1982 | Dorre et al. | 623/23 |
| 4,883,491 | 11/1989 | Mallory et al. | 623/23 X |

FOREIGN PATENT DOCUMENTS

| 3006178 | 7/1981 | Fed. Rep. of Germany. |
| 3538346 | 5/1987 | Fed. Rep. of Germany. |
| 3542016 | 6/1987 | Fed. Rep. of Germany. |
| A059919 | 9/1954 | France ............................ 623/23 |

Primary Examiner—Ronald Frinks
Attorney, Agent, or Firm—Merchant & Gould

[57] ABSTRACT

Presented is an endoprosthesis for the partial replacement of the joint head of a human bone, in particular of the thigh bone, that includes a first spherical segment whose diameter corresponds to the upper part of the natural joint head. Serving for anchoring the endoprosthesis in the human bone is an anchoring part that adjoins the first spherical segment and that is constructed as a second spherical segment that is capable of being anchored in a corresponding spherical recess in the bone.

12 Claims, 3 Drawing Sheets

PROSTHESIS FOR PARTIALLY REPLACING THE JOINT HEAD OF A HUMAN BONE

The invention concerns an endoprosthesis for the partial replacement of the joint head of a human bone, in particular of the thigh bone, with a first spherical segment whose diameter corresponds to that of the natural joint head, and with an anchoring part on the spherical segment.

These types of endoprostheses are known in particular as a partial replacement of the joint head of human thigh bones, and, for example, from German Patent 976,768, they make resection of the entire joint head necessary and have as an anchoring part a shaft that is anchored in the femur, in particular in the bone marrow cavity of the femur.

Known from Swiss Patent 602,091 is an endoprosthesis of this type that likewise can be implanted only after resection of the entire joint head and that is attached by means of two tension rods that run through the femur in the direction of the neck of the femur.

Disadvantageous in the case of these known endoprostheses is that the entire joint head must always be removed for their implantation and, indeed, even when only the upper running surface of the joint head is damaged, e.g. by coxathrosis. Additionally, anchoring of the anchoring part requires removal of additional bone material, whereby the natural femur experiences weakening.

Further known are cap-shaped endoprostheses that require merely milling off a thin layer of bone of the joint head and/or that even without any milling—with a certain amount of excess—are placed upon the joint head and firmly cemented there. Actually, in the case of these cap-shaped endoprostheses, bony material is removed only very sparsely, but since the diseased bone tissue has, as a rule, extended relatively far into the joint head, there exists the danger that diseased bony material will remain under the cap and, therefore, carries along with it further destruction of the joint head, pain and premature removal of the cap. Additionally, when using bone cement, there exists the danger that the bony material adjacent to the cement layer will be destroyed by the development of heat from the cement as it sets.

The object of the invention is to further develop an endoprosthesis of the initially-mentioned type such that the endoprosthesis, with careful but extensive resection of the natural bony material, has a firm anchoring.

This objective is met in accordance with the invention in the case of the endoprosthesis of the initially-mentioned type by the fact that the anchoring part is constructed as a second spherical segment whose surface displays an adhesive structure. The endoprosthesis in accordance with the invention has an anchoring part in the form of a spherical segment. To anchor the endoprosthesis in accordance with the invention, needing to be resected is merely a part of the joint head that corresponds to the first spherical segment. The underlying part of the joint head is retained; milled in this lower part of the joint head is then a spherical recess corresponding to the second spherical segment, which accommodates and anchors the spherical anchoring part of the endoprosthesis. The adhesive structure on the anchoring part assures that the anchoring part will maintain a sufficient rotational stability in the spherical recess and, therefore, will not be capable of turning when stressing.

The advantages of the invention lie particularly in the fact that only part of the joint head is totally resected, that by subsequent milling out of the spherical recess any malignant bone tissue also present in the depth of the head will be removed, that, on the other hand, however, the cortical material in the lower region of the joint head, and in particular at the neck of the head, will be completely preserved and be available as a supporting substance for the endoprosthesis. By this means, the endoprosthesis in accordance with the invention offers considerable advantages, in particular in those cases in which only the running surface of the joint head is damaged by disease, because only one part of the joint head is replaced by the first spherical segment, and the endoprosthesis is anchored by means of the second spherical segment in a relatively small anchoring recess. The neck of the head, as well as the part of the bone located thereunder is undisturbed by the implantation, the operation runs off carefully, the maximal available bone is retained.

In accordance with a preferred form of embodiment of the invention, the adhesive structure has on the surface of the anchoring part some outwardly-directed stems or nubs or spikes that press into the adjoining bony material and then reliably prevent movement of the endoprosthesis. Alternatively, the anchoring part can also display recesses, borings etc., into which can later grow bony material in order to increase the anchoring of the endoprosthesis.

Particularly preferred, the adhesive structure can also have on the anchoring part a layer of hydroxylapatite ceramic that enables and promotes intergrowth with the adjacent bone tissue.

In accordance with a particularly preferred form of embodiment of the invention, the second spherical segment, which represents the anchoring part, has a reduced diameter relative to the first spherical segment, and preferably passes over into the first spherical segment by means of a jump in diameter, so that there is formed between the first and the second spherical segment a circular supporting border that can support itself on the resection edge of the remaining lower joint head part. In this form of embodiment of the invention, the circular resection edge of the natural bone, together with the surface of the spherical anchoring part, accommodates the stresses transferred from the natural or artificial joint pan, the hard cortical material of the bone therewith remaining available for accepting the load.

For purposes of implantation, the endoprostheses in accordance with the invention must, in each case, be held available in different diameters for the first spherical segment and for the second spherical segment, in order to enable adapting the first spherical segment to the diameter of the natural joint head, and adapting the second spherical segment—depending upon the dimensions of the patient bone—to the different spherical recess in the patient bone. In order to limit the inventory and/or the diameter steps to a comfortable number, planned in accordance with the invention is to construct the first spherical segment and the second spherical segment as separate parts that can be joined with one another by means of a suitable connector, e.g. a conical plug-in connector. It is then possible to implant the second spherical segment with the suitable diameter—after resection of the upper part of the joint head —in a suitable size and next to select the first spherical segment with a suitable diameter and, for example, to anchor it firmly with the second spherical segment before or during the implantation by means of a conical plug-in connector. For realization of a conical plug-in connector, the first spherical segment can, for example, be joined with a conical pin on its contact surface, the second spherical segment then has on its contact surface a corresponding conical boring for the clamping-acceptance of the conical pin. Alternatively, however, other connecting elements for connecting the two separate spherical segments are possible.

Another preferred from of embodiment of the invention has a second spherical segment 6 that is flattened at its lower end and—relative to the first spherical segment 4—has a plane end area. Formed on the second spherical segment is preferably an external thread running about the axis of rotation, which forms the adhesive structure and permits a screwed anchoring of the endoprosthesis in the spongy tissue of the natural femur. The external thread has a diameter that is smaller than that of the first spherical segment, so that the spherical anchoring part can cut with its external thread into the spongy tissue of the femur without destroying the bone wall. To increase the degree of anchorage of the endoprosthesis, it is preferably possible to provide a boring in the second spherical segment that runs concentrically to the axis of rotation. Additionally, the wall of the second spherical segment can be pierced toward the boring so that the prosthesis intergrows by later-growing spongy tissue.

Advantageous further developments of the invention are characterized by the features of the subclaims.

Explained in more detail in the following with the aid of the drawing is an example of embodiment of the invention.

Figure 1:
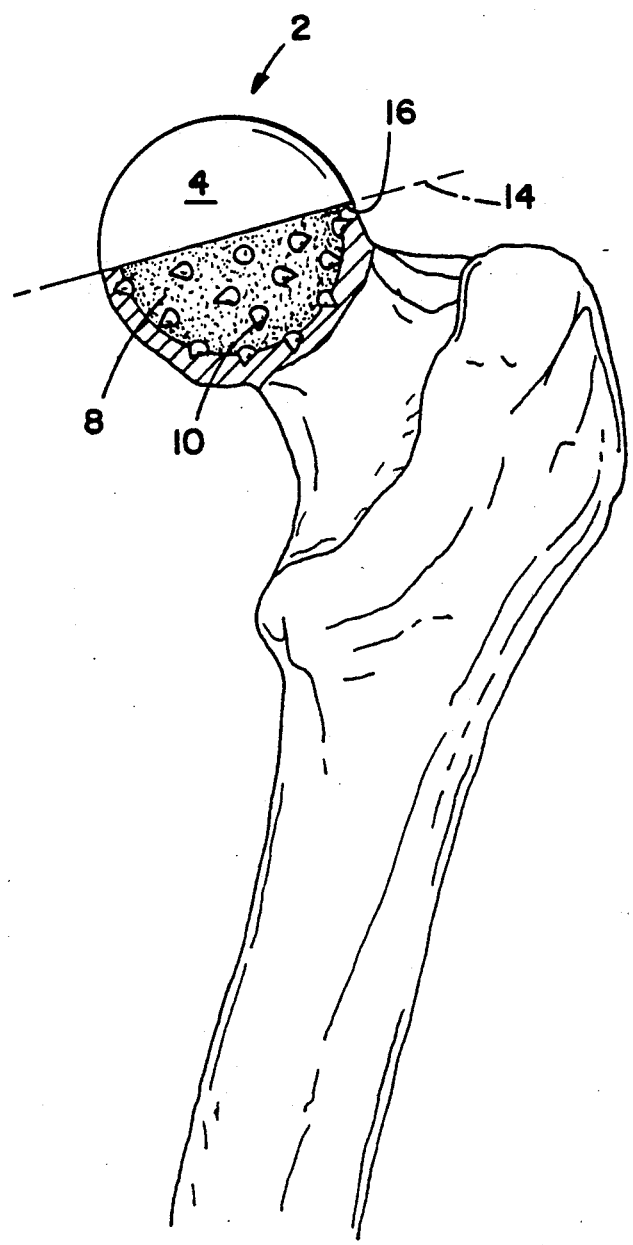
FIG. 1 shows a first form of embodiment of the endoprosthesis in the implanted condition.
Figure 2:
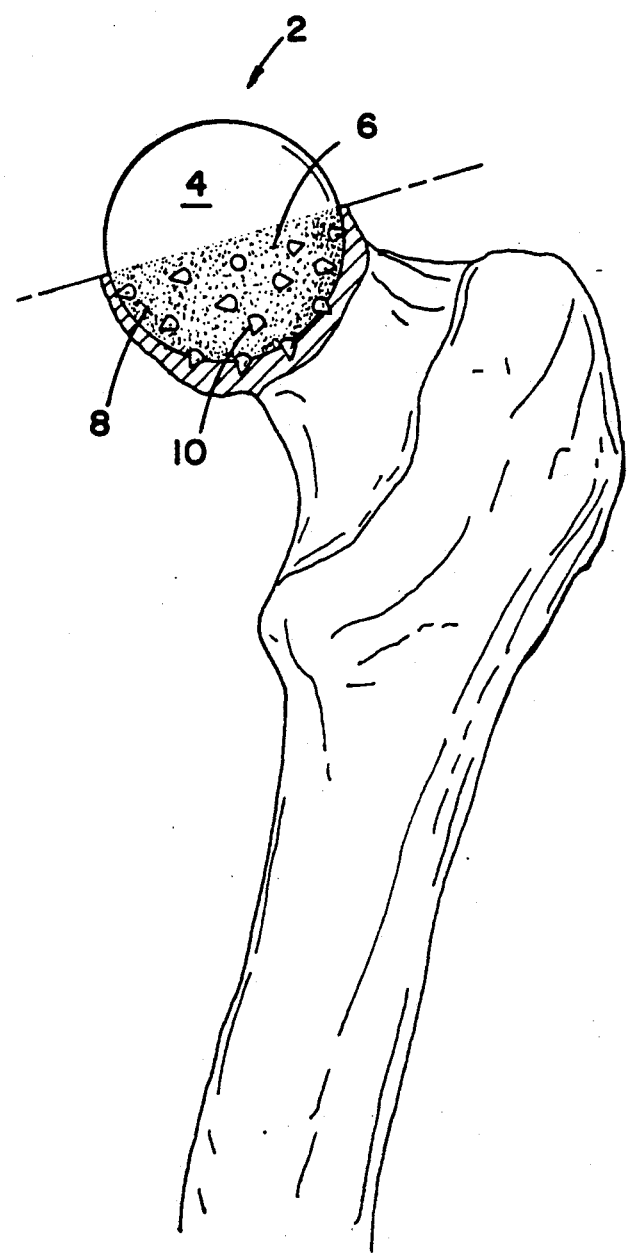
FIG. 2 shows a second form of embodiment of the endoprosthesis in the implanted condition.

Represented in FIG. 1 and 2 are two different forms of embodiment of the endoprosthesis in the implanted condition. The endoprosthesis 2 has a first spherical segment 4 whose diameter corresponds to the top, resected part of the natural joint head, and that replaces the upper part of the natural joint head. Adjoining the first spherical segment 4 is an anchoring part that is constructed as a second spherical segment 6 and displays on the surface an adhesive structure 8 which, for example, consists of outwardly-directed spikes or nubs, and moreover has a coating of hydroxylapatite ceramic.

In the case of the endoprosthesis represented in FIG. 1, the second spherical segment 6 has a reduced diameter relative to the first spherical segment 4 and passes over by means of a jump in diameter, e.g. in a common meridian plane 14, into the first spherical segment 4. The diameter step between the first and the second spherical segment 4, 6 represents a supporting edge 16 that lies on the cortical rim of the lower, unresected part of the joint head and supports the prosthesis. Additionally, the second spherical segment is supported in a corresponding spherical bone recess, particularly when the later-growing bone tissue again fills in any possibly open spaces present.

FIG. 2 shows an endoprosthesis that likewise has a first spherical segment 4 whose diameter corresponds to that of the upper part of the natural joint head. Provided as an anchoring part is a second spherical segment 6 whose surface is provided with an adhesive structure, e.g. nubs, stems or spikes and/or hydroxylapatite ceramic. In comparison to the form of embodiment in accordance with FIG. 1, the second spherical segment 6 has the same diameter as the first spherical segment 4. The spherical recess in the lower part of the joint head is then placed into the bone such that remaining on the resection edge is only a narrow resection rim, the endoprosthesis supporting itself only via the surface of the second spherical segment 6 in the spherical recess of the bone.

Figure 3:
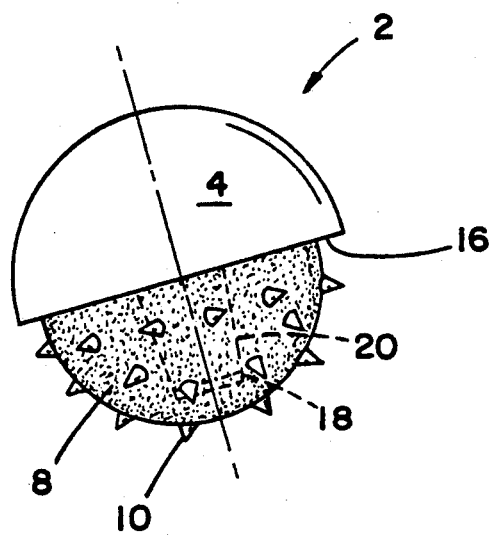
FIG. 3 shows a third form of embodiment of the endoprosthesis.

FIG. 3 shows a form of embodiment of the endoprosthesis corresponding to that of FIG. 1, where the first spherical segment and the second spherical segment 6 are constructed as separate parts that are firmly joinable with one another by means of a conical plug-in connector 18, 20. On the contact surface between the two spherical segments, the first spherical segment 4 has a conical stub 18 that can be introduced in clamping fashion into a corresponding conical boring 20 in the second spherical segment 6.

Figure 4:
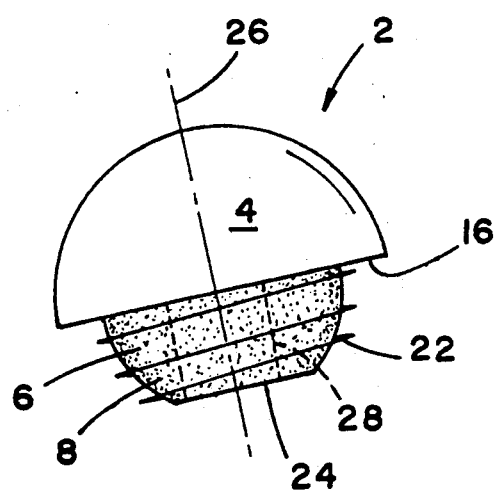
FIG. 4 shows a fourth form of embodiment of the endoprosthesis.

FIG. 4 shows a fourth form of embodiment of the endoprosthesis, where the second spherical segment 6—relative to the first spherical segment 4—displays a flat end area 24. On the second spherical segment 6, running about the axis of rotation 26, is an external thread 22 whose diameter is smaller than the spherical diameter of the first spherical segment 4. Further provided concentrically to the axis of rotation 26 is a boring 28 into which spongy tissue can grow. Further represented is a coating of the surface of the second spherical segment 6 with hydroxylapatite 8.

I claim:

1. Endoprosthesis for the partial replacement of the joint head of a human bone, in particular of the thigh bone, with a first spherical segment whose diameter corresponds to that of the natural joint head, and with an anchoring part on the spherical segment, characterized by the fact that the anchoring part is constructed as a second spherical segment (6) whose surface displays an adhesive structure (8).

2. Endoprosthesis according to claim 1, characterized by the fact that the adhesive structure (8) contains outwardly-directed spikes or nubs (10).

3. Endoprosthesis according to claim 1, characterized by the fact that the second spherical segment (6) has a boring (28).

4. Endoprosthesis according claim 1, characterized by the fact that the adhesive structure (8) contains a layer of hydroxylapatite.

5. Endoprosthesis according to claim 1, characterized by the fact that the second spherical segment (6) displays a reduced diameter relative to the first spherical segment (4).

6. Endoprosthesis according to claim 5, characterized by the fact that the two spherical segments (4, 6) have a common middle point (12) and extend from opposite sides up to a common meridian plane (14).

7. Endoprosthesis according to claim 1, characterized by the fact that the endoprosthesis consists of two separate parts that are joinable by means of a connector.

8. Endoprosthesis according to claim 7, characterized by the fact that the first spherical segment (4) is a separate part, and that the second spherical segment (6) is a separate part.

9. Endoprosthesis according to claim 7, characterized by the fact that the connection between the separate parts is formed as a plug-in conical connector.

10. Endoprosthesis according to claim 1, characterized by the fact that the second spherical segment (6), relative to the first spherical segment (4), has one flat end surface (24).

11. Endoprosthesis according to claim 1, characterized by the fact that formed on the second spherical segment (6) is an external thread (22) running about the external surface of said second spherical segment.

12. Endoprosthesis according to claim 11, characterized by the fact that the outermost external edge of the external thread (22) lies within a spherical area having a smaller diameter than the first spherical segment (4).

* * * * *